United States Patent [19]

Young et al.

[11] Patent Number: 5,331,000
[45] Date of Patent: Jul. 19, 1994

[54] ANTIPYRETIC AND ANALGESIC METHODS AND COMPOSITIONS CONTAINING OPTICALLY PURE R(−) KETOPROFEN

[75] Inventors: James W. Young, Palo Alto, Calif.; Nancy M. Gray, Marlborough, Mass.; William J. Wechter, Redlands, Calif.

[73] Assignee: Sepracor Inc., Marlborough, Mass.

[21] Appl. No.: 24,728

[22] Filed: Mar. 1, 1993

Related U.S. Application Data

[63] Continuation-in-part of Ser. No. 848,458, Mar. 9, 1992, abandoned.

[51] Int. Cl.$^5$ .............................................. A61K 31/19
[52] U.S. Cl. .................................................. 514/570
[58] Field of Search ........................................ 514/570

[56] References Cited

U.S. PATENT DOCUMENTS

| | | | |
|---|---|---|---|
| 3,641,127 | 2/1972 | Farge et al. | 260/516 |
| 4,868,214 | 9/1989 | Sunshine et al. | 514/568 |
| 4,927,854 | 5/1990 | Sunshine et al. | 514/570 |
| 4,962,124 | 10/1990 | Sunshine et al. | 514/568 |
| 4,973,745 | 11/1990 | Blaschke et al. | 562/401 |
| 5,057,427 | 10/1991 | Wald et al. | 435/280 |
| 5,114,714 | 5/1992 | Young et al. | 424/400 |
| 5,114,715 | 5/1992 | Young et al. | 424/400 |

FOREIGN PATENT DOCUMENTS 0419312  3/1991  European Pat. Off.
WO90/1579  12/1990  PCT Int'l Appl.

OTHER PUBLICATIONS

March, *Advanced Organic Chemistry*, 2nd. ed., "Methods of Resolution & Optical Purity", 1977, pp. 108–113.

Brune et al., "Aspirin-like Drugs May Block Pain Independently of Prostaglandin Synthesis Inhibition," *Experientia* 47: 257–261 (1991).

Honda et al., "Studies on the Metabolic Fate of Etodolac, (IV), Stereoselective Disposition of Etodolac in Rats," *Iyakuhin Kenkyu* 22(1): 147–151 (1991).

Brocks and Jamali, "The Pharmacokinetics of Etodolac Enantiomers in the Rat," *Drug Metabolism and Disposition* 18(4): 471–475 (1990).

Geisslinger et al., "Pharmacokinetics of S(+) and R(−) Ibuprofen in Rheumatoid Arthritis," *European Journal of Clinical Pharmacology* 38(5): 493–497 (1990).

Jamali et al., "Ketoprofen Pharmacokinetics in Humans: Evidence of Enantiomeric Inversion and Lack of Interaction," *Journal of Pharmaceutical Sciences* 79(5): 460–461 (1990).

Knihinicki et al., "Stereoselective Disposition of Ibuprofen and Flurbiprofen in Rats," *Chirality* 2: 134–140 (1990).

Muller et al., "Pharmacological Aspects of Chiral Nonsteroidal Anti-Inflammatory Drugs," *Fundam Clin Pharmacol* 4: 617–634 (1990).

Murray and Brater, "Nonsteroidal Anti-Inflammatory Drugs," *Clinical Pharmacology* 6(2): 365–397 (1990).

Sumi et al., "Acute Toxicity Study of Metabolites, Degradation Products, Impurity and Optical Isomers of Etodolac in Mice," *Pharmacometrics (Oyo-Yakuri)* 40(6): 737–746 (1990).

Williams, "Enantiomers in Arthritic Disorders," *Pharmac. Ther.* 46: 273–295 (1990).

(List continued on next page.)

*Primary Examiner*—Marianne M. Cintins
*Assistant Examiner*—William R. A. Jarvis
*Attorney, Agent, or Firm*—Pennie & Edmonds

[57] ABSTRACT

Methods and compositions are disclosed utilizing optically pure R(−) ketoprofen for the treatment of pain including, but not limited to, pain associated with toothaches, headaches, sprains, joint pain and post-surgical pain, for example dental pain and ophthalmic pain, while substantially reducing adverse effects including, but not limited to, gastrointestinal, renal and hepatic toxicities, and leukopenia, which are associated with the administration of racemic ketoprofen. Optically pure R(−) ketoprofen is also useful in treating pyrexia while substantially reducing the adverse effects associated with the administration of racemic ketoprofen.

14 Claims, No Drawings

OTHER PUBLICATIONS

Jamali et al., "Enantioselective Aspects of Drug Action and Disposition: Therapeutic Pitfalls," *Journal of Pharmaceutical Sciences* 78(9): 695-715 (1989).

Stechter, Handbook of Stereoisomers: Therapeutic Drugs, *CRC Press Inc.* 137-147 (1989).

Caldwell et al., "The Metabolic Chiral Inversion and Dispositional Enantioselectivity of the 2-Arylpropionic Acids and Their Biological Consequences," *Biochemical Pharmacology* 37(1): 105-114 (1988).

Foster et al., "Pharmacokinetics of Ketoprofen Enantiomers in Healthy Subjects Following Single and Multiple Doses," *Journal of Pharmaceutical Sciences* 77(1): 70-73 (1988).

Foster et al., "Pharmacokinetics of Ketoprofen Enantiomers in Young and Elderly Arthritic Patients Following Single and Multiple Doses," *Journal of Pharmaceutical Sciences* 77(3): 191-195 (1988).

Jamali, "Pharmacokinetics of Enantiomers of Chiral Non-Steroidal Anti-Inflammatory Drugs," *European Journal of Drug Metabolism and Pharmacokinetics* 13(1): 1-9 (1988).

Jamali et al., "Stereoselective Pharmacokinetics of Flurbiprofen in Humans and Rats," *Journal of Pharmaceutical Sciences* 77(8): 666-669 (1988).

Williams and Day, "The Contribution of Enantiomers to Variability in Response to Anti-Inflammatory Drugs," *Anti-Rheumatic Drugs AAS* 24: 76-84 (1988).

Abas and Meffin, "Enantioselective Disposition of 2-Arylpropionic Acid Nonsteroidal Anti-Inflammatory Drugs. IV/Ketoprofen Disposition," *The Journal of Pharmacology and Experimental Therapeutics* 240(2): 637-641 (1987).

Yamaguchi et al., "The Inhibitory Activities of 4580156-S and its Related Compounds on Prostaglandin Synthetase," *Nippon Yakuriguky Zasshi* 90: 295-302 (with English abstract) (1987).

Humber et al., "Etodolac (1,8-Diethyl-1,3,4,9-tetrahydropyranol [3,4-6]indole-1-acetic Acid): A Potent Anti-Inflammatory Drug. Conformation and Absolute Configuration of its Active Enantiomer," *J. Med. Chem.* 29: 871-874 (1986).

Singh et al., "Pharmacokinetics of the Enantiomers of Tiaprofenic Acid in Humans," *Journal of Pharmaceutical Sciences* 75(5): 43914 442 (1986).

Williams and Day, "Stereoselective Disposition-Basis for Variability in Response to NSAID's," *Non-Steroidal Anti-Inflammatory Drugs Basis for Variability in Response AAS* 17: 119-126 (1985).

Hutt and Caldwell, "The Importance of Stereochemistry in the Clinical Pharmacokinetics of the 2-Arylpropionic Acid Non-Steroidal Anti-Inflammatory Drugs," *Clinical Pharmacokinetics* 9: 371-373 (1984).

Tamassia et al., "Pharmacokinetics of the enantiomers of Indoprofen in Man," *Int. J. Clin. Pharm. Res.* IV(3): 223-230 (1984).

Demerson et al., "Resolution of Etodolac and Anti-Inflamatory and Prostaglandin Synthetase Inhibiting Properties of the Enantiomers," *J. Med. Chem.* 26: 1778-1780 (1983).

Hutt and Caldwell, "The Metabolic Chiral Inversion of 2-arylprionic Acids-A Novel Route with Pharmacological Consequences," *J. Pharm. Pharmacol.* 35: 693-704 (1983).

ANTIPYRETIC AND ANALGESIC METHODS AND COMPOSITIONS CONTAINING OPTICALLY PURE R(−) KETOPROFEN

This application is a continuation-in-part of application Ser. No. 07/848,458, filed Mar. 9, 1992 now abandoned.

BACKGROUND OF THE INVENTION

This invention relates to novel compositions of matter containing optically pure R(−) ketoprofen. These compositions possess potent activity in treating pain including but not limited to, pain associated with toothaches, headaches, sprains, joint pain and surgical pain, for example dental pain and ophthalmic pain, while substantially reducing adverse effects associated with the administration of the racemic mixture of ketoprofen including but not limited to gastrointestinal, renal and hepatic toxicities, as well as leukopenia. Additionally, these novel compositions of matter containing optically pure R(−) ketoprofen are useful in treating or preventing pyrexia while substantially reducing the adverse effects associated with the administration of the racemic ketoprofen. Also disclosed are methods for treating the above-described conditions in a human while substantially reducing the adverse effects that are associated with the racemic mixture of ketoprofen, by administering the R(−) isomer of ketoprofen to said human.

The active compound of these compositions and methods is an optical isomer of ketoprofen. Ketoprofen is described in U.S. Pat. No. 3,641,127. Chemically, the active compound is the R(−) isomer of 2-(3-benzoylphenyl)propionic acid, hereinafter referred to as R(−) ketoprofen. The term "R(−) isomer of ketoprofen" and particularly the term "R(−) ketoprofen" encompass optically pure and substantially optically pure R(−) ketoprofen.

Ketoprofen, which is the subject of the present invention, is available commercially only as the 1:1 racemic mixture. That is, ketoprofen is available only as a mixture of optical isomers, called enantiomers.

Steric Relationship and Drug Action

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are mirror images of one another. A specific stereoisomer may also be referred to as an enantiomer, and a mixture of such isomers is often called an enantiomeric or racemic mixture.

Stereochemical purity is of importance in the field of pharmaceuticals, where 12 of the 20 most prescribed drugs exhibit chirality. A case in point is provided by the L-form of the beta-adrenergic blocking agent, propranolol, which is known to be 100 times more potent than the D-enantiomer.

Furthermore, optical purity is important since certain isomers may actually be deleterious rather than simply inert. For example, it has been suggested that the D-enantiomer of thalidomide was a safe and effective sedative when prescribed for the control of morning sickness during pregnancy, while the corresponding L-enantiomer has been believed to be a potent teratogen.

Ketoprofen, which is illustrated in FIG. I, is a nonsteriodal antiinflammatory drug ("NSAID") which is known to inhibit the biosynthesis of prostaglandins by the inhibition of the cyclooxygenase enzyme which is ubiquitous in mammalian tissues.

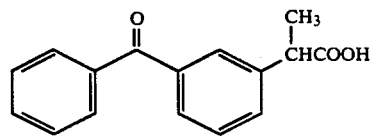

Ketoprofen

Fig. I

The enantiomers of ketoprofen are disclosed in Yamaguchi et al., *Nippon Yakurigaku Zasshi*. 90: 295-302 (1987). This reference states that the S-enantiomers of 2-arylpropionic acids have 15-300 times higher prostaglandin synthetase inhibitory activities than the R-enantiomers in the rat. Additionally, the S-enantiomer of ketoprofen is disclosed in U.S. Pat. Nos. 4,868,214, 4,962,124, and 4,927,854. Each of these patents alleges that the analgesic activity of ketoprofen resides exclusively in the S(+) enantiomers, an allegation that stands in sharp contrast to the present invention.

The enantiomers of ketoprofen are also disclosed in Abas et al., *J. Pharmacol. Exp. Ther.*, 240: 637-641 (1987). This reference states that R-ketoprofen is metabolically converted to S-ketoprofen in the rabbit. In man, such inversion has been suggested to occur only to a small extent. See Jamali et al., *J. Pharm. Sci.*, 79: 460-461 (1990). Jamali et al. teach that the pharmacological activity of ketoprofen is assumed to reside in the S-enantiomer and that interconversion of the R-enantiomer to the S-enantiomer is possibly clinically insignificant.

Furthermore, Caldwell et al., *Biochem. Pharmacol.* 37: 105-114 (1988) state that the interconversion of R-2-arylpropionic acids to S-2-arylpropionic acids is a phenomenon that has been suggested to occur for a variety of 2-arylpropionic acids. Caldwell et al. also teach that the combination of chiral inversion and stereoselective metabolism provides for a more rapid clearance of the R-enantiomers of 2-arylpropionic acids. Additionally, Caldwell et al. allege that "at best, the R-isomers function as prodrugs for the therapeutically active S-forms" when the racemic drug is administered and thus add to both the therapeutic and toxic effects of the active S-enantiomers. This reference further contends that "at worst, the R-enantiomers are undesirable impurities in the active drug" causing difficulties due to non-stereoselective toxicity. Thus the reference alleges that the use of only the S-isomers should provide safer and more effective use of this class of drugs.

Similarly, it has been generalized that the pharmacokinetics of the enantiomers of 2-arylpropionic acids are different due, at least in part, to the unidirectional metabolic inversion of the R to the S enantiomer. However, it has been found that this interconversion depends on the particular compound and the particular species in which it is administered. Jamali, *Eur. J. Drug Metabolism Pharmaco.* 13(1): 1–9 (1988).

The racemic mixture of ketoprofen is presently used primarily as an analgesic agent in treating pain, including but not limited to pain associated with toothaches, headaches, sprains, joint pain and surgical pain, for example dental pain (e.g., after periodontal surgery) and ophthalmic pain (e.g., after cataract surgery).

Pain is a common symptom, reflecting either physical (i.e., the result of tissue injury or inflammation) or emotional discomfort. Pain is a complex subjective phenomenon comprised of a sensation reflecting real or potential tissue damage, and the affective response this generates. Pain may be classified as either acute or chronic, and it is of a variety of particular types. Acute pain is an essential biologic signal of the potential for, or the extent of, tissue injury. In contrast, chronic pain is physically and psychologically debilitating, and it no longer serves its adaptive biologic role. In many patients, organic disease may be insufficient to explain the degree of pain. Chronic pain may be associated with conditions including but not limited to osteoarthritis, rheumatoid arthritis, soft tissue pain syndromes, and headaches.

Pyrexia, or fever, is an elevation in body temperature as a result of infection, tissue damage, inflammation, graft rejection, malignancy or other disease states. The regulation of body temperature requires a delicate balance between the production and loss of heat. The hypothalamus regulates the target point at which body temperature is maintained. In fever, this target point is elevated; antipyretic compositions promote its return to a normal level.

Many of the NSAIDs cause somewhat similar adverse effects. These adverse effects include but are not limited to gastrointestinal, renal and hepatic toxicities. The administration of the racemic mixture of ketoprofen has been found to cause these, as well as other adverse effects. These other adverse effects include but are not limited to increases in bleeding times due to disruption of platelet function (e.g., thrombocytopenia), and prolongation of gestation due to uterine effects.

Further, leukopenia (decreased white cell count in the blood) is a known side effect of NSAIDs. Agranulocytosis is an acute disease caused by a precipitous drop in the number of white blood cells. The leukopenia/agranulocytosis syndrome has been described for several NSAIDs, such as indomethacin, ketoprofen, and ibuprofen. Indeed, such NSAIDs are contraindicated in patients whose immune systems are compromised by HIV infection, chemotherapy, ionizing irradiation, corticosteroids, immunosuppressives, etc. or by such conditions as emphysema, bronchiectasis, diabetes mellitus, leukemia, burns and the like. Although the overall incidence is low, agranulocytosis is a life-threatening syndrome that develops very rapidly. Periodic white-cell counts are therefore of little help in providing early warning of this syndrome.

Thus, it would be particularly desirable to find a compound with the advantages of the racemic mixture of ketoprofen which would not have the aforementioned disadvantages.

SUMMARY OF THE INVENTION

It has now been discovered that the optically pure R(−) isomer of ketoprofen (see FIG. II below) is a potent analgesic that substantially reduces adverse effects associated with the administration of the racemic mixtures of ketoprofen, including but not limited to gastrointestinal, renal and hepatic toxicities, increases in bleeding times, leukopenia, and prolongation of gestation. It has also been discovered that these novel compositions of matter containing optically pure R(−) ketoprofen are useful in treating or preventing pyrexia while substantially reducing the above-described adverse effects associated with the administration of racemic ketoprofen. The present invention also includes methods for treating the above-described conditions in a human while substantially reducing the adverse effects that are associated with the racemic mixture of ketoprofen by administering the optically pure R(−) isomer of ketoprofen to said human.

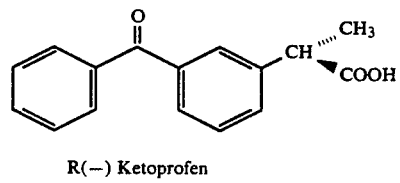

R(−) Ketoprofen

Fig. II

DETAILED DESCRIPTION OF THE INVENTION

The present invention encompasses a method of eliciting an analgesic effect in a human, while substantially reducing the concomitant liability of adverse effects associated with the administration of racemic ketoprofen, which comprises administering to a human in need of analgesic therapy, an amount of R(−) ketoprofen, or a pharmaceutically acceptable salt thereof, substantially free of its S(+) stereoisomer, said amount being sufficient to alleviate pain, but insufficient to cause the adverse effects associated with racemic mixture of ketoprofen.

The present invention also encompasses an analgesic composition for the treatment of a human in need of analgesic therapy, which comprises an amount of R(−) ketoprofen, or a pharmaceutically acceptable salt thereof, substantially free of its S(+) stereoisomer, said amount being sufficient to alleviate pain but insufficient to cause the adverse effects associated with racemic ketoprofen.

The present invention further encompasses a method of treating or preventing pyrexia in a human, while substantially reducing the concomitant liability of adverse effects associated with the administration of racemic ketoprofen, which comprises administering to a human an amount of R(−) ketoprofen or a pharmaceutically acceptable salt thereof, substantially free of its S(+) stereoisomer, said amount being sufficient to alleviate or prevent said pyrexia but insufficient to cause adverse effects associated with the administration of racemic ketoprofen.

In addition, the present invention encompasses an antipyretic composition for the treatment of a human in need of such therapy which comprises an amount of R(−) ketoprofen or a pharmaceutically acceptable salt thereof, substantially free of its S(+) stereoisomer, said amount being sufficient to alleviate or prevent said pyrexia but insufficient to cause adverse effects associated with the administration of racemic ketoprofen.

The available racemic mixture of ketoprofen (i.e., a 1:1 mixture of the two enantiomers) possesses analgesic and antipyretic activity; however, this racemic mixture while offering the expectation of efficacy, causes adverse effects. Utilizing the substantially optically pure or optically pure R(−) isomer of ketoprofen results in clearer dose related definitions of efficacy, diminished adverse effects, and accordingly, an improved therapeutic index. It is therefore, more desirable to use the R(−) isomer of ketoprofen than racemic ketoprofen.

The term "adverse effects" includes, but is not limited to gastrointestinal, renal and hepatic toxicities, leukopenia, increases in bleeding times due to, e.g., thrombocytopenia, and prolongation of gestation. The term "gastrointestinal toxicities" includes but is not limited to gastric and intestinal ulcerations and erosions. The term "renal toxicities" includes but is not limited to such conditions as papillary necrosis and chronic interstitial nephritis.

In one embodiment the term "substantially free of its S(+) isomer" as used herein means that the composition contains at least 90% by weight of R(−) ketoprofen and 10% by weight or less of the corresponding S(+) ketoprofen. In a preferred embodiment the term "substantially free of the S(+) stereoisomer" means that the composition contains at least 99% by weight of R(−) ketoprofen and 1% or less of the corresponding S(+) ketoprofen. In the most preferred embodiment, the term "substantially free of its S(+) stereoisomer" as used herein means that the composition contains greater than 99% by weight of R(−) ketoprofen and less than 1% of the corresponding S(+) ketoprofen. These percentages are based upon the total amount of ketoprofen present in the composition. The terms "substantially optically pure R(−) isomer of ketoprofen" or "substantially optically pure R(−) ketoprofen" and "optically pure R(−) ketoprofen" or "optically pure R(−) isomer of ketoprofen" are also encompassed by the above-described amounts.

The term "eliciting an analgesic effect" as used herein means treating, relieving, ameliorating or preventing mild to moderate pain. For example, such pain includes but is not limited to pain associated with toothaches, headaches, sprains, joint pain, surgical pain, dental pain, and ophthalmic pain.

The term "pyrexia" as used herein means the elevation of body temperature brought about by disorders including but not limited to infectious disease, tissue damage, inflammation, graft rejection, malignancy or other disease states.

The chemical synthesis of the racemic mixture of ketoprofen can be performed by the method described in U.S. Pat. No. 3,641,127 which is hereby incorporated by reference.

The R(−) isomer of ketoprofen may be obtained from its racemic mixture by resolution of the enantiomers using conventional means such as an optically active resolving base. See, for example, U.S. Pat. Nos. 4,983,765 and 4,973,745, the disclosures of which are incorporated herein by reference. Additionally, the optically pure R-isomer of ketoprofen can be prepared from the corresponding acrylic acid by catalytic hydrogenation using a chiral catalyst. See, for example, European Patent Application No. EP 90/402,433 and WO 90/015,790, the disclosures of which are also incorporated herein by reference. Furthermore, the optically pure R-isomer of ketoprofen can be prepared from the racemic mixture by enzymatic biocatalytic resolution. See, for example, U.S. Pat. Nos. 5,057,427 and 5,077,217, the disclosures of which are incorporated herein by reference.

The magnitude of a prophylactic or therapeutic dose of R(−) ketoprofen in the acute or chronic management of disease will vary with the severity of the condition to be treated, and the route of administration. The dose, and perhaps the dose frequency, will also vary according to the age, body weight, and response of the individual patient. In general, the total daily dose range for R(−) ketoprofen, for the conditions described herein, is from about 25 mg to about 2000 mg, in single or divided doses. Preferably, a daily dose range should be between about 200 mg to about 1000 mg, in single or divided doses. In managing the patient, the therapy should be initiated at a lower dose, perhaps about 25 mg to about 200 mg and increased up to about 1000 mg or higher depending on the patient's global response. It is further recommended that infants, children, patients over 65 years, and those with impaired renal or hepatic function, initially receive low doses, and that they be titrated based on individual response(s) and blood level(s). It may be necessary to use dosages outside these ranges in some cases as will be apparent to those skilled in the art. Further, it is noted that the clinician or treating physician would know how and when to interrupt, adjust or terminate therapy in conjunction with individual patient response. The terms "an amount sufficient to alleviate pain but insufficient to cause said adverse effects" and "an amount sufficient to alleviate or prevent pyrexia but insufficient to cause said adverse effects" are encompassed by the above-described dosage amounts and dose frequency schedule.

Any suitable route of administration may be employed for providing the patient with an effective dosage of R(−) ketoprofen. For example, oral, rectal, transdermal, parenteral (subcutaneous, intramuscular, intravenous), intrathecal, and like forms of administration may be employed. Dosage forms include tablets, troches, dispersions, suspensions, solutions, capsules, patches, and the like.

The pharmaceutical compositions of the present invention comprise R(−) ketoprofen as the active ingredient, or a pharmaceutically acceptable salt thereof, and may also contain a pharmaceutically acceptable carrier, and optionally, other therapeutic ingredients.

The terms "pharmaceutically acceptable salts" or "a pharmaceutically acceptable salt thereof" refer to salts prepared from pharmaceutically acceptable non-toxic acids or bases including inorganic acids and bases and organic acids and bases. Since the compound of the present invention is acidic, salts may be prepared from pharmaceutically acceptable non-toxic bases including inorganic and organic bases. Suitable pharmaceutically acceptable base addition salts for the compound of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine.

The compositions of the present invention include compositions such as suspensions, solutions, elixirs, and aerosols. Carriers such as starches, sugars, microcrystalline cellulose, diluents, granulating agents, lubricants, binders, disintegrating agents, and the like may be used in the case of oral solid preparations. Oral solid preparations (such as, powders, capsules, and tablets) are preferred over the oral liquid preparations. The most preferred oral solid preparation is tablets. If desired, tablets may be coated by standard aqueous or nonaqueous techniques.

In addition to the common dosage forms set out above, the compounds of the present invention may also be administered by controlled release means and/or delivery devices such as those described in U.S. Pat. Nos.: 3,845,770; 3,916,899; 3,536,809; 3,598,123; and 4,008,719, the disclosures of which are hereby incorporated by reference in their entireties.

Pharmaceutical compositions of the present invention suitable for oral administration may be presented as discrete units such as capsules, cachets, or tablets, or aerosol sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding, in a suitable machine, a mixture of the powdered compound moistened with an inert liquid diluent. Desirably, each tablet contains from about 12.5 mg to about 1000 mg of the active ingredient, and each cachet or capsule contains from about 12.5 mg to about 600 mg of the active ingredient. Most preferably, the tablet, cachet or capsule contains either one of three dosages, about 50 mg, about 100 mg and about 200 mg of the active ingredient.

The invention is further defined by reference to the following examples describing the preparation of the compositions of the present invention, as well as their utility. It will be apparent to those skilled in the art that many modifications, both to materials and methods, may be practiced without departing from the purpose and interest of this invention.

EXAMPLES

EXAMPLE 1

Preparation of R(−) Ketoprofen

The following is a description of the resolution of racemic ketoprofen by an enzymatic process. Included is a description of the synthesis of the water-soluble ester used (a three step procedure), as well as the actual enzymatic resolution, subsequent base hydrolysis, and the recovery of R(−) ketoprofen acid.

A. Synthesis of Ketoprofen Dimethylethanolamine Ester

Racemic ketoprofen (0.5 moles) was added to thionyl chloride (1.0 moles) in a flask fitted with a drying tube. Dimethylformamide (0.25 mL) was added to the reaction mixture and the mixture was stirred and warmed until the ketoprofen dissolved and gas evolution commenced. The heat was removed and the mixture was stirred at room temperature for 18 hours. The thionyl chloride was removed under reduced pressure and the oily residue of acid chloride slowly solidified.

The acid chloride was dissolved in tetrahydrofuran (125 mL) and added to a solution of N,N-dimethylethanolamine (1.0 moles) in tetrahydrofuran (500 mL) cooled to 0° C. in a flask equipped with a drying tube. After the addition, the reaction mixture was stirred at room temperature for 18 hours. A saturated aqueous solution of potassium carbonate (500 mL) was added to the reaction mixture and the resulting organic layer was removed. The aqueous layer was extracted with diethyl ether (2×250 mL) and the organic layers were combined, washed with a saturated aqueous solution of sodium chloride, dried over potassium carbonate and the solvent removed under reduced pressure. The product was isolated as a colorless viscous oil.

B. Quaternization of the N,N-Dimethylethanolamine Ester

The resulting N,N-dimethylethanolamine ester was dissolved in diethyl ether (500 mL) and cooled to 0° C. A solution of dimethyl sulfate (0.36 moles) in diethyl ether (500 mL) was added to the cooled solution and the resulting solution was stirred at room temperature for 18 hours. The resulting solid material was removed by filtration, washed with diethyl ether and dried under vacuum to yield the N,N,N-trimethylethanolammonium ester of ketoprofen (ketoprofen choline ester) as a white solid.

C. Enzymatic Transesterification of the Racemic Ketoprofen Choline Ester

The choline ester (0.36 moles) was dissolved in 0.2M sodium phosphate buffer (900 ml, pH 7.0). To this solution was added methanol (100 mL) and Protease type XXVII (3 gm) which is available commercially from sigma Chemical Co. The reaction was allowed to stir gently at room temperature for 24 hours. The reaction mixture was extracted with diethyl ether (2×250mL) and the organic layer was reserved. The aqueous layer was adjusted to pH 2 by the addition of concentrated sulfuric acid and the resulting mixture was washed with ether (2×150 mL). The aqueous layer was concentrated under reduced pressure and the volume was adjusted to 900 mL by the addition of 0.2M sodium phosphate buffer (pH 7.0). To this solution was added methanol (100 mL) and Protease type XXVII (2 gm). The reaction was allowed to stir gently at room temperature for 24 hours. The reaction mixture was extracted with diethyl ether (2×250mL) and this organic layer was combined with the layer reserved from the first enzymatic reaction. The combined ether layers were dried over magnesium sulfate and the solvent removed under reduced pressure to leave crude R(−) ketoprofen methyl ester, which was dried under vacuum.

D. Preparation of R(−) Ketoprofen

The crude ester was combined with ethanolic potassium hydroxide solution (pH 13) and the resulting mixture was stirred for 1 hour at room temperature.

The resulting solution was adjusted to pH 2 by the addition of hydrochloric acid. The resulting mixture was extracted with diethyl ether and the combined ether solutions were dried over magnesium sulfate and the solvent removed under reduced pressure to leave crude R(−) ketoprofen. The crude acid was recrystallized from diethyl ether to yield R(−) ketoprofen.

EXAMPLE 2

The phenylquinone writhing test is a standard procedure for detecting and comparing analgesic activity in laboratory animals, and generally correlates well with human efficacy. In response to an injected, locally irritating solution, the animals have cramps ("writhings") that are inhibited by analgesic agents.

Mice were first dosed with at least two dose levels each of R(−) ketoprofen, S(+) ketoprofen, and racemic ketoprofen. The mice were then challenged with a solution of phenyl-p-benzoquinone given intraperitoneally and observed for the characteristic stretch-writhing syndrome. Lack of writhing is indicative of analgesic activity. The degree of analgesic activity was calculated on the basis of suppression of writhing relative to control animals tested the same day. Time response data were obtained by challenging the mice with the phenylquinone solution at different time intervals after dosing them with the test medications.

In this test, 100% of the animals demonstrated at least a 50% reduction in the number of writhings after 3 mg/kg oral dosing with either R(−) ketoprofen or S(+) ketoprofen. All animals were tested one hour after drug administration. The analgesic effects in this test were found to be dose-dependent.

A complicating factor when studying the pharmacological effects of R(−) and S(+) ketoprofen in some animals is that R(−) ketoprofen is inverted into S(+) ketoprofen by a hepatic enzymatic pathway. One hour after the oral administration of R(−) ketoprofen in mice, approximately 39% of the circulating drug is inverted into the S(+) form. (Such inversion does not occur in man.)

EXAMPLE 3

Toxicity

The following is a description of a study of the effects of the isomers of ketoprofen in the guinea pig. Groups of 6–10 guinea pigs are dosed orally with either vehicle, racemic ketoprofen (20, 10, 5, 1 and 0.1 mg/kg), S(+) ketoprofen (20, 10, 5, 1 and 0.1 mg/kg), and R(−) ketoprofen (20, 10, 5, 1 and 0.1 mg/kg). Within 24 hours after the dose, the animals are euthanized and gross abnormalities are recorded in the GI tracts, with particular attention to the gastric muscosa of the stomach. Microerosions and redness (irritations) are noted, and the effects are compared between the treatment groups as described by Aberg & Larsson (Acta Pharmacol. Toxicol. 28: 249–257, 1970). Based on such observations, the R(−) isomer is seen to cause virtually no gastrointestinal irritation.

EXAMPLE 4

Leukopenia

To test white-cell survival, an in vitro test method is used, where a primary bone marrow cell culture is exposed to increasing concentrations of test compounds such as R(−) ketoprofen and S(+) ketoprofen. A known inducer of leukopenia, such as thiouracil, is used as a positive control. The survival of the granulocytes is measured using conventional differential cell-counting methodology.

The risk for leukopenic effects of escalating concentrations of drugs in vivo is studied in groups of animals in which a mild granulocytopenia has initially been induced either by drugs such as thiouracil or chloramphenicol, or by radiation. Repeated white-cell counts are performed to monitor the development of leukopenia in the animals.

EXAMPLE 5

Inhibitory Effect on the Activity of Cyclooxygenase

It is a well-known fact that cyclooxygenase inhibitors (for example aspirin and indomethacin) cause damage and irritation of the gastric muscosa.

Assays to determine the inhibitory effect of R(−), S(+), and racemic ketoprofen, reference agents and vehicles on cyclooxygenase activity are conducted using RBL-1 cells (rat basophilic leukemia cell line). The effects of the test compounds, reference agents or vehicles are assessed on the cyclooxygenase-mediated production of $PGF_{2-alpha}$.

RBL-1 cells are grown in culture in Eagles's minimum essential medium supplemented with 12% fetal bovine serum and 1:100 antibiotic/antimycotic mixture at 37° C. Cells are harvested via centrifugation, washed with cold phosphate buffered saline (PBS), and suspended in PBS supplemented with 0.88 uM $CaCl_2$. Cells are incubated in the presence of a screening concentration of test compound or reference agent. Alternatively, cells are incubated in the presence of vehicle.

Following the incubation period, cyclooxygenase activity is stimulated by the addition of 5uM of a calcium ionophore to the incubation medium. The reaction is terminated by chilling the tubes on ice.

The cells are then separated via centrifugation, and the supernatant is removed. Aliquots of the supernatant are used to measure the calcium-ionophore-stimulated production of $PGF_{2-alpha}$ via radioimmunoassay.

For each experiment, a vehicle-control is evaluated. A reference standard is also evaluated at a single concentration with each assay.

EXAMPLE 6

| Oral Formulation Capsules: Formula | | | |
|---|---|---|---|
| | Quantity per capsule in mg | | |
| Active ingredient | A | B | C |
| R(−) Ketoprofen | 50.0 | 100.0 | 200.0 |
| Lactose | 48.5 | 148.5 | 48.5 |
| Titanium Dioxide | 0.5 | 0.5 | 0.5 |
| Magnesium Stearate | 1.0 | 1.0 | 1.0 |
| Compression Weight | 100.0 | 250.0 | 250.0 |

The active ingredient, R(−) ketoprofen, is sieved and blended with the excipients. The mixture is filled into suitably sized two-piece hard gelatin capsules using suitable machinery. Other doses may be prepared by altering the fill weight and if necessary, changing the capsule size to suit.

What is claimed is:

1. A method of eliciting an analgesic effect with reduced gastrointestinal toxicity in a human, comprising administering to said human a therapeutically effective analgesic amount of R(−) ketoprofen or a pharmaceutically acceptable salt thereof, substantially free of its S(+) stereoisomer.

2. The method of claim 1 wherein R(−) ketoprofen is administered by intrathecal or intravenous infusion, transdermal delivery, or orally as a tablet or a capsule.

3. The method of claim 3 wherein the amount of R(−) ketoprofen or a pharmaceutically acceptable salt thereof administered is from about 25 mg to about 2000 mg per day.

4. The method of claim 4 wherein the amount administered is from about 200 mg to about 1000 mg per day.

5. The method of claim 1 wherein the amount of R(−) ketoprofen or a pharmaceutically acceptable salt thereof is greater than approximately 90% by weight of the total weight of ketoprofen.

6. The method of claim 1 wherein the amount of said R(−) ketoprofen or a pharmaceutically acceptable salt thereof, substantially free of the S(+) stereoisomer, is administered together with a pharmaceutically acceptable carrier.

7. The method of claim 1 wherein R(−) ketoprofen is administered as a salt selected from the group consisting of sodium, calcium and lysinate salts.

8. A method of treating pyrexia with reduced gastrointestinal toxicity in a human, comprising administering to said human a therapeutically effective antipyretic amount of R(−) ketoprofen or a pharmaceutically acceptable salt thereof, substantially free of its S(+) stereoisomer.

9. The method of claim 8 wherein R(−) keotprofen is administered by intrathecal or intravenous infusion, transdermal delivery, or orally as a tablet or a capsule.

10. The method of claim 9 wherein the amount of R(−) keotprofen administered is from about 25 mg to about 2000 mg per day.

11. The method of claim 10 wherein the amount administered is from about 200 mg to about 1000 mg per day.

12. The method of claim 8 wherein the amount of R(−) keotprofen or a pharmaceutically acceptable salt thereof, is greater than approximately 90% by weight of the total weight of ketoprofen.

13. The method of claim 8 wherein the amount of R(−) ketoprofen or a pharmaceutically acceptable salt thereof, substantially free of the S(+) stereoisomer, is administered together with a pharmaceutically acceptable carrier.

14. The method according of claim 8 wherein R(−) ketoprofen is administered as a salt selected from the group consisting of sodium, calcium and lysinate salts.

* * * * *

UNITED STATES PATENT AND TRADEMARK OFFICE
CERTIFICATE OF CORRECTION

PATENT NO. : 5,331,000

DATED : July 19, 1994

INVENTOR(S) : James W. Young, Nancy M. Gray and William J. Wechter

It is certified that error appears in the above-indentified patent and that said Letters Patent is hereby corrected as shown below:

Column 12, line 1 (claim 9): "keotprofen" should be --ketoprofen--;

Column 12, line 5 (claim 10): "keotprofen" should be --ketoprofen--;

Column 12, line 11 (claim 12): "keotprofen" should be --ketoprofen--.

Signed and Sealed this

Twenty-fifth Day of October, 1994

Attest:

BRUCE LEHMAN

Attesting Officer     Commissioner of Patents and Trademarks

UNITED STATES PATENT AND TRADEMARK OFFICE
Certificate

Patent No. 5,331,000                                                                                                Patented: July 19, 1994

On motion pursuant to 37 C.F.R. § 1.634 in Interference No. 103,979, it has been found that the above identified patent, through error and without any deceptive intent, improperly sets forth the inventorship.

Accordingly, pursuant to 35 U.S.C. § 256 it is hereby certified that the correct inventorship of this patent is: James W. Young and William J. Wechter.

Signed and Sealed this Sixteenth Day of February, 1999.

MARY F. DOWNEY
*Administrative Patent Judge*
Board of Appeals and Interferences